(12) United States Patent  
Macatangay et al.

(10) Patent No.: US 10,610,393 B2  
(45) Date of Patent: Apr. 7, 2020

(54) WIRE RETENTION AND RELEASE MECHANISMS

(71) Applicant: COOK MEDICAL TECHNOLOGIES LLC, Bloomington, IN (US)

(72) Inventors: Edwin Macatangay, Bloomington, IN (US); Joseph Erik Hughes, Cincinnati, OH (US)

(73) Assignee: Cook Medical Technologies LLC, Bloomington, IN (US)

( * ) Notice: Subject to any disclaimer, the term of this patent is extended or adjusted under 35 U.S.C. 154(b) by 188 days.

(21) Appl. No.: 15/467,115

(22) Filed: Mar. 23, 2017

(65) Prior Publication Data

US 2017/0273812 A1 Sep. 28, 2017

Related U.S. Application Data

(60) Provisional application No. 62/312,755, filed on Mar. 24, 2016.

(51) Int. Cl.
*A61F 2/966* (2013.01)
*A61F 2/954* (2013.01)
(Continued)

(52) U.S. Cl.
CPC ............... *A61F 2/966* (2013.01); *A61F 2/01* (2013.01); *A61F 2/04* (2013.01); *A61F 2/06* (2013.01);
(Continued)

(58) Field of Classification Search
CPC .. A61F 2/954; A61F 2/966; A61F 2002/9517;
A61F 2/01; A61F 2/04; A61F 2/06; A61F 2/07; A61F 2/24; A61F 2/2475; A61F 2/82; A61F 2002/011; A61F 2002/041; A61F 2002/044;
(Continued)

(56) References Cited

U.S. PATENT DOCUMENTS 5,387,235 A 2/1995 Chuter
5,693,083 A 12/1997 Baker et al.
(Continued)

FOREIGN PATENT DOCUMENTS

| EP | 2 066 269 B1 | 2/2012 |
| WO | WO 98/11846 A1 | 3/1998 |
| WO | WO 98/53761 A1 | 12/1998 |

OTHER PUBLICATIONS

Partial European Search Report for related Application No. EP 17275039.0, dated Oct. 12, 2017, 9 pgs.

*Primary Examiner* — George J Ulsh
(74) *Attorney, Agent, or Firm* — Brinks Gilson & Lione (57) ABSTRACT

Devices for delivering and deploying a prosthesis are disclosed and comprise a sheath, a prosthesis disposed within a distal end portion of the sheath, and a wire having a first end coupled to the prosthesis and a second end coupled to the sheath. A body portion of the wire comprises a slack in the wire, and the sheath, prosthesis, and wire are configured so that a proximal movement of the sheath relative to the prosthesis reduces the slack in the wire, and a subsequent proximal movement of the sheath relative to the prosthesis decouples the wire from the prosthesis. Additional devices, systems, and methods are disclosed.

18 Claims, 7 Drawing Sheets

(51) Int. Cl.
*A61F 2/01* (2006.01)
*A61F 2/04* (2013.01)
*A61F 2/06* (2013.01)
*A61F 2/07* (2013.01)
*A61F 2/24* (2006.01)
*A61F 2/82* (2013.01)
*A61F 2/95* (2013.01)

(52) U.S. Cl.
CPC .................. *A61F 2/07* (2013.01); *A61F 2/24* (2013.01); *A61F 2/2475* (2013.01); *A61F 2/82* (2013.01); *A61F 2/954* (2013.01); *A61F 2002/011* (2013.01); *A61F 2002/041* (2013.01); *A61F 2002/044* (2013.01); *A61F 2002/046* (2013.01); *A61F 2002/048* (2013.01); *A61F 2002/061* (2013.01); *A61F 2002/9517* (2013.01); *A61F 2002/9665* (2013.01)

(58) Field of Classification Search
CPC .......... A61F 2002/046; A61F 2002/048; A61F 2002/061; A61F 2002/9665
See application file for complete search history.

(56) References Cited

U.S. PATENT DOCUMENTS

| | | |
|---|---|---|
| 5,755,777 A | 5/1998 | Chuter |
| 5,776,142 A | 7/1998 | Gunderon |
| 5,873,906 A | 2/1999 | Lau et al. |
| 6,346,118 B1 | 2/2002 | Baker et al. |
| 6,416,499 B2 | 7/2002 | Paul, Jr. |
| 6,524,335 B1 | 2/2003 | Hartley et al. |
| 6,939,370 B2 | 9/2005 | Hartley et al. |
| 6,984,244 B2 | 1/2006 | Perez et al. |
| 7,105,020 B2 | 9/2006 | Greenberg et al. |
| 7,232,459 B2 | 6/2007 | Greenberg et al. |
| 7,335,224 B2 | 2/2008 | Ohlenschlaeger |
| 7,435,253 B1 | 10/2008 | Hartley et al. |
| 7,488,344 B2 | 2/2009 | Hartley et al. |
| 7,537,606 B2 | 5/2009 | Hartley et al. |
| 7,611,529 B2 | 11/2009 | Greenberg et al. |
| 7,637,932 B2 | 12/2009 | Bolduc et al. |
| 7,651,519 B2 | 1/2010 | Dittman |
| 7,666,219 B2 | 2/2010 | Rasmussen et al. |
| 7,691,139 B2 | 4/2010 | Baker et al. |
| 7,722,657 B2 | 5/2010 | Hartley |
| 7,780,717 B2 | 8/2010 | Ducke et al. |
| 7,803,177 B2 | 9/2010 | Hartley et al. |
| 7,823,267 B2 | 11/2010 | Bolduc |
| 7,828,838 B2 | 11/2010 | Bolduc et al. |
| 7,846,194 B2 | 12/2010 | Hartley et al. |
| 7,998,186 B2 | 8/2011 | Hartley |
| 7,998,189 B2 | 8/2011 | Kolbel et al. |
| 8,012,193 B2 | 9/2011 | Hartley et al. |
| 8,114,145 B2 | 2/2012 | Hartley et al. |
| 8,241,346 B2* | 8/2012 | Chobotov ............... A61F 2/962 606/108 |
| 8,394,135 B2 | 3/2013 | Jensen et al. |
| 8,414,636 B2 | 4/2013 | Nabulsi et al. |
| 8,475,514 B2 | 7/2013 | Hartley et al. |
| 8,500,792 B2 | 8/2013 | Berra |
| 8,506,616 B2 | 8/2013 | Hartley et al. |
| 8,523,933 B2 | 9/2013 | Nabulsi et al. |
| 8,709,060 B2 | 4/2014 | Osborne |
| 8,753,385 B2 | 6/2014 | Hartley et al. |
| 8,758,425 B2 | 6/2014 | Greenberg et al. |
| 8,808,349 B2 | 8/2014 | Chuter et al. |
| 8,845,708 B2 | 9/2014 | Hartley et al. |
| 8,876,879 B2 | 11/2014 | Hartley et al. |
| 8,968,380 B2 | 3/2015 | Nimgaard |
| 9,060,895 B2 | 6/2015 | Hartley et al. |
| 9,132,024 B2 | 9/2015 | Brinser |
| 2001/0012944 A1 | 8/2001 | Bicek et al. |
| 2002/0151953 A1* | 10/2002 | Chobotov ............... A61F 2/954 623/1.11 |
| 2004/0098084 A1 | 5/2004 | Hartley et al. |
| 2005/0171479 A1 | 8/2005 | Hruska et al. |
| 2007/0078395 A1 | 4/2007 | Valaie |
| 2007/0088424 A1 | 4/2007 | Greenberg et al. |
| 2007/0123910 A1 | 5/2007 | Hartley et al. |
| 2008/0082154 A1* | 4/2008 | Tseng ........................ A61F 2/07 623/1.11 |
| 2008/0082158 A1* | 4/2008 | Tseng ........................ A61F 2/07 623/1.13 |
| 2009/0099638 A1 | 4/2009 | Grewe |
| 2011/0034987 A1 | 2/2011 | Kennedy |
| 2011/0118816 A1 | 5/2011 | Jensen et al. |
| 2011/0125249 A1 | 5/2011 | Jensen et al. |
| 2011/0230947 A1 | 9/2011 | Hartley et al. |
| 2012/0203325 A1* | 8/2012 | Weisman ................... A61F 2/95 623/1.12 |
| 2012/0290068 A1 | 11/2012 | Roeder et al. |
| 2012/0323300 A1 | 12/2012 | Greenberg et al. |
| 2013/0131775 A1 | 5/2013 | Hadley et al. |
| 2013/0289696 A1 | 10/2013 | Maggard et al. |
| 2014/0058402 A1 | 2/2014 | Havel |
| 2014/0114392 A1 | 4/2014 | McDonald et al. |
| 2014/0121755 A1 | 5/2014 | Farag et al. |
| 2014/0236277 A1 | 8/2014 | Greenberg et al. |
| 2014/0257453 A1 | 9/2014 | Roeder |
| 2014/0257464 A1 | 9/2014 | Roeder |
| 2014/0277330 A1 | 9/2014 | Roeder |
| 2014/0277348 A1 | 9/2014 | Roeder |
| 2014/0277349 A1 | 9/2014 | Vad |
| 2014/0277350 A1 | 9/2014 | Melsheimer |
| 2014/0277355 A1 | 9/2014 | Roeder |
| 2015/0164669 A1 | 6/2015 | Parker, Jr. et al. |

* cited by examiner

WIRE RETENTION AND RELEASE MECHANISMS

CROSS-REFERENCE TO RELATED APPLICATIONS

This application claims the benefit of the filing date under 35 U.S.C. § 119 (e) of U.S. Provisional Patent Application Ser. No. 62/312,755, filed Mar. 24, 2016, which is hereby incorporated by reference.

TECHNICAL FIELD

This application relates generally to medical devices, systems, and methods. More particularly, this application describes devices, systems, and methods for retaining and delivering an endoluminal prosthesis in a body.

BACKGROUND

Throughout the specification, when referring to an endovascular prosthesis, the terms "proximal" and "proximally" shall denote a position, direction, or orientation that is generally toward, or in the direction of, a patient's heart. The terms "distal" and "distally" shall denote a position, direction, or orientation that is generally opposite "proximal" or "proximally," or in a direction away from the heart.

Conversely, when referring to any portion of a device or system for delivering an endovascular prosthesis, the terms "proximal" and "proximally" shall denote a position, direction, or orientation that is generally toward, or in the direction of, the operator of the device or system. The terms "distal" and "distally" shall denote a position, direction, or orientation that is generally opposite "proximal" or "proximally," or in a direction toward, or in the direction of, the patient.

Various techniques have been proposed for delivering and deploying an endoluminal prosthesis in a patient from a remote location. For example, U.S. Pat. No. 5,387,235, entitled "Expandable Transluminal Graft Prosthesis for Repair of Aneurysm," discloses containing a prosthesis (e.g., a stent graft for treating aortic aneurysms) within a distal portion of an outer sheath. The outer sheath is used to introduce the prosthesis into a patient's vasculature from a remote location in the patient's body (e.g., the patient's arms or legs), and to carry the prosthesis through the vasculature to the area to be treated. When the prosthesis is positioned at a desired site, the outer sheath may then be withdrawn to release the prosthesis. These and other features disclosed in U.S. Pat. No. 5,387,235 could be used with the present invention, and the disclosure of this patent is herewith incorporated in its entirety into this specification.

PCT Patent Publication No. WO 98/53761, entitled "A Prosthesis And A Method And Means Of Deploying A Prosthesis," discloses devices for introducing endoluminal prostheses within an external sleeve. The publication discloses proximal and distal attachment devices that may be attached to the proximal and/or distal ends of the prosthesis, respectively. The attachment devices enable selective releasing of the proximal and distal ends of the prosthesis. These and other features disclosed in PCT Patent Publication No. WO 98/53761 could be used with the present invention, and the disclosure of this publication is herewith incorporated in its entirety into this specification.

Figure 1:
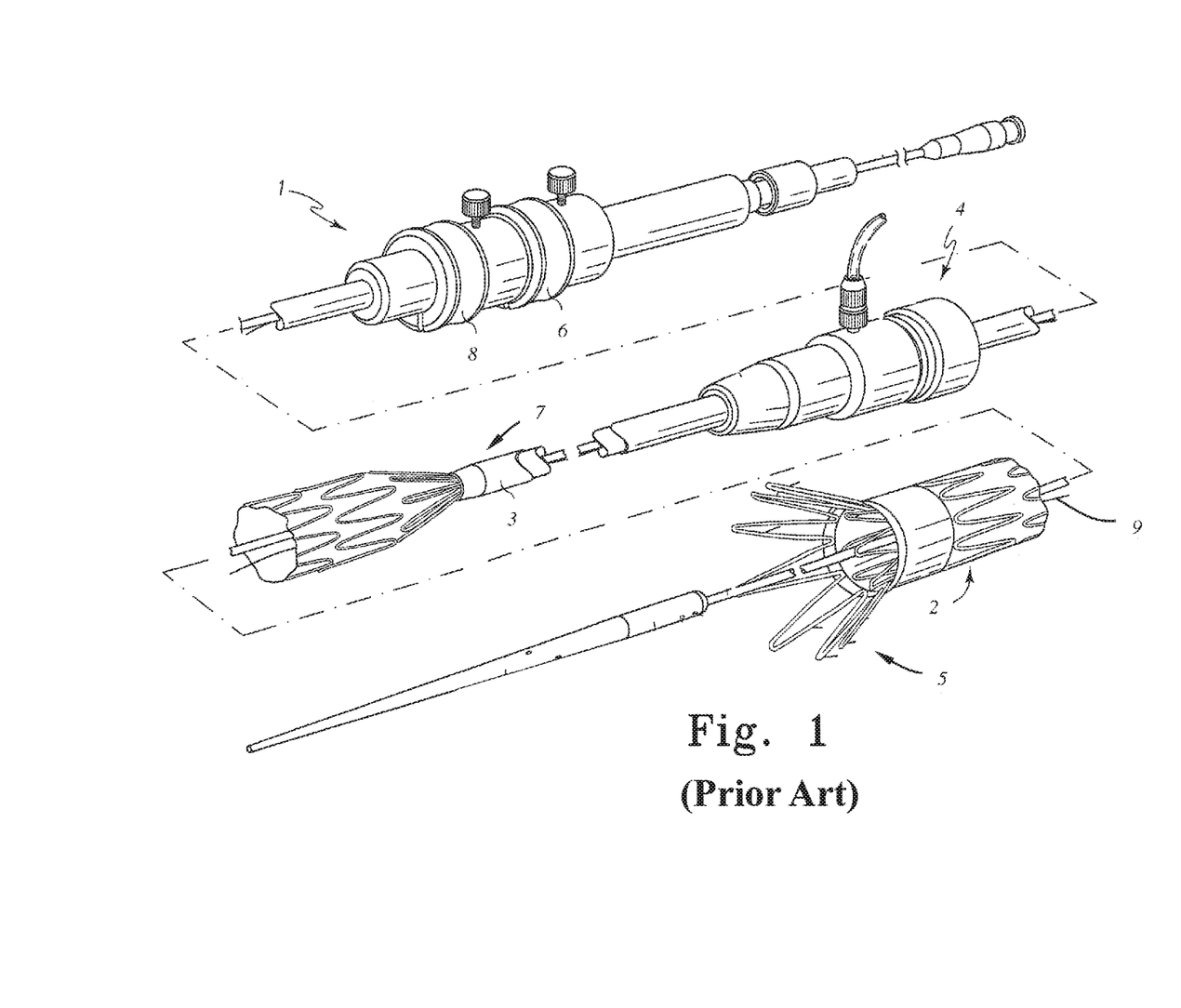
FIG. 1 depicts a prior art device for delivering and deploying an endoluminal prosthesis.

U.S. Pat. No. 7,666,219, entitled "Prosthesis Deployment System Retention Device," also discloses devices for introducing endoluminal prostheses. FIG. 1 of the present application depicts an introducer 1 in accordance with the teachings of U.S. Pat. No. 7,666,219. The introducer 1 includes a prosthesis 2 retained in a compressed condition by a sheath 3, which extends proximally to handle 4. Proximal and distal retention devices retain proximal and distal portions of the prosthesis, respectively. The proximal retention device includes a trigger wire 9 coupled to a proximal portion 5 of the prosthesis and extending proximally from the prosthesis to trigger wire release mechanism 6. The distal retention device includes a trigger wire (not shown) coupled to a distal portion 7 of the prosthesis and extending proximally from the prosthesis to trigger wire release mechanism 8. The prosthesis 2 is released from the sheath 3 by pulling proximally on the sheath 3 via handle 4 to uncover the prosthesis 2. The trigger wires are released from the proximal and distal portions of the prosthesis 2 by removing the proximal and distal release mechanisms 6, 8, respectively. These and other features disclosed in U.S. Pat. No. 7,666,219 could be used with the present invention and the disclosure of this patent is herewith incorporated in its entirety into this specification.

Additional examples of catheter delivery systems utilizing wire release mechanisms are described in U.S. Pat. Nos. 6,524,335, 6,939,370, 7,335,224, 7,435,253, 7,537,606, 7,611,529, 7,651,519, 7,722,657, 7,803,177, 8,012,193, 8,394,135, 8,506,616, 8,709,060, 8,845,708, and 8,968,380, and in U.S. Patent Publication Nos. 2004/0230287 A1, 2007/0043425 A1, 2008/0294234 A1, and 2014/0277330 A1. The disclosure of each of these references is herewith incorporated in its entirety into this specification.

In the known trigger wire release systems, the trigger wires are manually removed from the prosthesis, independently of the sheath and in multiple steps. In order to release the prosthesis depicted in FIG. 1, for example, U.S. Pat. No. 7,666,219 describes a process including: 1) withdrawing sheath 3 to uncover a portion of the prosthesis; 2) removing the proximal trigger wire release mechanism 6 to release the proximal trigger wire from the prosthesis; 3) withdrawing the sheath 3 to further uncover the prosthesis; and 4) removing the distal wire release mechanism 8 to release the distal trigger wire from the prosthesis. Although such systems are suitable for their intended use, there is room for improvement. There is a need in the art for delivery and deployment systems with simple, intuitive to use wire retention and release mechanisms.

SUMMARY

The present application describes prosthesis delivery and deployment devices comprising a sheath having a proximal end, a distal end, and a lumen extending therebetween; a prosthesis disposed within a distal end portion of the sheath; and a wire having a first end coupled to the prosthesis, a second end coupled to the sheath, and a body portion disposed between the first and second ends of the wire. The body portion of the wire may comprise a slack in the wire. The sheath, prosthesis, and wire may be configured so that a proximal movement of the sheath relative to the prosthesis reduces the slack in the wire, and a subsequent proximal movement of the sheath relative to the prosthesis decouples the wire from the prosthesis. As so configured, a proximal movement of the sheath relative to the prosthesis may perform multiple tasks, including withdrawing the sheath from the prosthesis and releasing the wire from the prosthesis.

In some examples, the second end of the wire may be coupled to a handle of the sheath disposed, for example, at the proximal end of the sheath. The handle may comprise a drum for storing and releasing the slack. In some examples, the slack may be wound about the drum and released by unwinding the wire from the drum. In some examples, the handle may comprise a haemostatic valve for controlling blood loss through the delivery and deployment device.

The prosthesis may be disposed entirely within the distal end of the sheath. Alternatively, the prosthesis may be disposed partially within the distal end of the sheath. In some examples, the slack in the wire may correspond with a length of the prosthesis. For example, the slack may correspond with approximately 10% or more, or 50% or more of the length of the prosthesis. In these examples, the sheath may be withdrawn proximally a distance approximately 10% or more, or approximately 50% or more of the length of the prosthesis before the slack in the wire is eliminated and the wire can decouple from the prosthesis.

In some examples, a delivery and deployment device may include at least a second wire having a first end coupled to the prosthesis, a second end coupled to the sheath, and a body portion between the first and second ends of the wire. The body portion of the second wire may comprise a slack in the second wire that is less than, generally equal to, or greater than the slack in the first wire. The sheath, prosthesis, and second wire may be configured so that a proximal movement of the sheath relative to the prosthesis reduces the slack in the second wire, and a subsequent proximal movement of the sheath relative to the prosthesis decouples the second wire from the prosthesis. In some examples, the sheath, prosthesis, first wire, and second wire may be configured so that: 1) a proximal movement of the sheath relative to the prosthesis reduces the slack in the first and second wires; 2) a first subsequent proximal movement of the sheath relative to the prosthesis decouples the first wire from the prosthesis and further reduces the slack in the second wire; and 3) a second subsequent proximal movement of the sheath relative to the prosthesis decouples the second wire from the prosthesis.

The first ends of the wires may be coupled to the prosthesis at the same general location of the prosthesis. Alternatively, the first ends of the wires may be coupled at different locations of the prosthesis. For example, the first end of one or more of the wires may be coupled to the proximal end of the prosthesis and the first end of another one or more of the wires may be coupled to the distal end of the prosthesis.

In some examples, a prosthesis delivery and deployment device may comprise a sheath having a proximal end, a distal end, and a lumen extending therebetween; a prosthesis disposed within a distal end portion of the sheath; and a wire having a first end coupled to the prosthesis, a second end coupled to the sheath, and a body portion disposed between the first and second ends, the body portion of the wire comprising a slack in the wire; where the wire is configured so that a proximal movement of the sheath relative to the prosthesis reduces the slack in the wire, and a subsequent proximal movement of the sheath relative to the prosthesis decouples the wire from the prosthesis.

The prosthesis delivery and deployment device of these examples comprises any two or more of the following: the second end of the first and/or second wires is coupled to a handle of the sheath; the second end of the first and/or second wires is coupled to a handle disposed at the proximal end of the sheath; the second end of the first and/or second wires is coupled to a handle comprising a drum, and the slack is wound about the drum; the second end of the first and/or second wires is coupled to a handle comprising a haemostatic valve; the prosthesis is disposed entirely within the distal end of the sheath; the slack of the first and/or second wires corresponds with a length of the prosthesis; the slack of the first and/or second wires corresponds with approximately 10% or more of the length of the prosthesis; the slack of the first and/or second wires corresponds with approximately 50% or more of the length of the prosthesis; the first wire slack and the second wire slack are generally equal; the second wire slack is greater than the first wire slack; the first end of one of the first and second wires is coupled to the proximal end of the prosthesis and the first end of the other of the second and first wires is coupled to the distal end of the prosthesis; and the sheath, prosthesis, first wire, and second wire are configured so that: 1) a proximal movement of the sheath relative to the prosthesis reduces the slack in the first and second wires, 2) a first subsequent proximal movement of the sheath relative to the prosthesis decouples the first wire from the prosthesis and further reduces the slack in the second wire, and 3) a second subsequent proximal movement of the sheath relative to the prosthesis decouples the second wire from the prosthesis.

The present application also describes prosthesis delivery and deployment devices comprising a sheath having a proximal end, a distal end, and a lumen extending therebetween; a haemostatic valve assembly coupled to the proximal end of the sheath; a prosthesis disposed within a distal end portion of the sheath; and a wire having a first end coupled to the prosthesis, a second end coupled to the valve assembly, and a body portion disposed between the first and second ends of the wire. The sheath, valve assembly, prosthesis, and wire may be configured so that proximal movement of the valve assembly relative to the prosthesis retracts the sheath and decouples the wire from the prosthesis.

In some examples, the body portion of the wire may comprise a slack in the wire, and the sheath, valve assembly, prosthesis, and wire may be configured so that a proximal movement of the valve assembly decouples the wire from the prosthesis. In some examples, the valve assembly may comprise a drum for storing and releasing the slack. In some examples, the slack may be wound about the drum and released by unwinding from the drum.

The prosthesis may be disposed entirely within the distal end of the sheath. Alternatively, the prosthesis may be disposed partially within the distal end of the sheath. In some examples, the slack in the wire may correspond with a length of the prosthesis. For example, the slack may correspond with approximately 10% or more, or 50% or more of the length of the prosthesis. In these examples, the sheath may be withdrawn proximally a distance approximately 10% or more, or approximately 50% or more of the length of the prosthesis before the slack in the wire is eliminated and the wire decouples from the prosthesis.

In some examples, a delivery and deployment device described above may include at least a second wire having a first end coupled to the prosthesis, a second end coupled to the valve assembly, and a body portion disposed between the first and second ends. The sheath, valve assembly, prosthesis, and second wire may be configured so that proximal movement of the valve assembly with respect to the prosthesis decouples the second wire from the prosthesis. The distal ends of the wires may be coupled at the same general location of the prosthesis. Alternatively, the distal ends of the wires may be coupled at different locations of the prosthesis. For example, the first end of one or more of the wires may be coupled to the proximal end of the prosthesis and the first end of another one or more of the wires may be coupled to the distal end of the prosthesis.

In some examples, a prosthesis delivery and deployment device may comprise a sheath having a proximal end, a distal end, and a lumen extending between the proximal and distal ends; a haemostatic valve assembly coupled to the proximal end of the sheath; a prosthesis disposed within a distal end portion of the sheath; a wire having a first end coupled to the prosthesis, a second end coupled to the valve assembly, and a body portion disposed between the first and second ends of the wire; where the sheath, valve assembly, prosthesis, and wire are configured so that proximal movement of the valve assembly relative to the prosthesis retracts the sheath and decouples the wire from the prosthesis.

The prosthesis delivery and deployment device of these examples comprises any two or more of the following: the body portion of the wire comprises a slack in the wire, and the sheath, valve assembly, prosthesis, and wire are configured so that a proximal movement of the valve assembly relative to the prosthesis reduces the slack in the wire, and a subsequent proximal movement of the valve assembly relative to the prosthesis decouples the wire from the prosthesis; a second wire having a first end coupled to the prosthesis, a second end coupled to the valve assembly, and a body portion disposed between the first and second ends, where the sheath, valve assembly, prosthesis, and second wire are configured so that proximal movement of the valve assembly decouples the second wire from the prosthesis; the body portion of the second wire comprises a slack in the wire, and the sheath, valve assembly, prosthesis, and wire are configured so that a proximal movement of the valve assembly relative to the prosthesis reduces the slack in the second wire, and a subsequent proximal movement of the valve assembly relative to the prosthesis decouples the second wire from the prosthesis; the first end of one of the first and second wires is coupled to the proximal end of the prosthesis and the first end of the other of the second and first wires is coupled to the distal end of the prosthesis; the second end of the first and/or second wires is coupled to a drum, and the slack is wound about the drum; the slack of the first and/or second wires corresponds with a length of the prosthesis; the slack of the first and/or second wires corresponds with approximately 10% or more of the length of the prosthesis; the slack of the first and/or second wires corresponds with approximately 50% or more of the length of the prosthesis; the first wire slack and the second wire slack are generally equal; the second wire slack is greater than the first wire slack; and the sheath, prosthesis, first wire, and second wire are configured so that: 1) a proximal movement of the valve assembly relative to the prosthesis reduces the slack in the first and second wires, 2) a first subsequent proximal movement of the valve assembly relative to the prosthesis decouples the first wire from the prosthesis and further reduces the slack in the second wire, and 3) a second subsequent proximal movement of the valve assembly relative to the prosthesis decouples the second wire from the prosthesis.

A prosthesis retention method is described and comprises the steps of: disposing a prosthesis within a distal end portion of a sheath; coupling a first end of a wire to the prosthesis and a second end of the wire to the sheath; and providing a slack in the wire between the first and second ends of the wire. Additional steps may include, for example, coupling a first end of a second wire to the prosthesis and a second end of the second wire to the sheath; providing a slack in the second wire between the first and second ends of the second wire; selecting a slack of the first wire and/or second wire that corresponds with a length of the prosthesis; and selecting a slack of the second wire that is less than, generally equal to, or greater than, the slack of the first wire.

A method of delivering and deploying a prosthesis is described and comprises the steps of providing a prosthesis delivery and deployment device including a sheath, a prosthesis, and one or more wires as disclosed in this specification; moving the sheath with respect to the prosthesis to withdraw the sheath from the prosthesis; and moving the sheath further to decouple the wire from the prosthesis. When the delivery and deployment device includes at least a first and second wire, the method may include the steps of: 1) moving the sheath with respect to the prosthesis to withdraw the sheath from the prosthesis; 2) moving the sheath further with respect to the prosthesis to decouple the first wire from the prosthesis; and then 3) moving the sheath further with respect to the prosthesis to decouple the second wire from the prosthesis.

DETAILED DESCRIPTION OF PREFERRED EMBODIMENTS

The embodiments described below relate to devices, systems, and methods for delivering and deploying an endoluminal prosthesis. The term "prosthesis" means any device, object, or structure that supports, repairs, or replaces, or is configured to support, repair, or replace a body part or a function of that body part. It can also mean a device that enhances or adds functionality to a physiological system. Examples of prostheses include, but are not limited to, stents, stent grafts, vena cava filters, occlusion devices, and the like.

Throughout the specification, unless the context requires otherwise, the words "comprise," "include," and "have," and variations such as "comprising," "including," and "having," imply the inclusion of an item or group of items, without the exclusion of any other item or group of items.

When referring to an endovascular prosthesis, the terms "proximal" and "proximally" shall denote a position, direction, or orientation that is generally toward, or in the direction of, a patient's heart. The terms "distal" and "distally" shall denote a position, direction, or orientation that is generally opposite "proximal" or "proximally," or in a direction away from the heart. Conversely, when referring to any portion of a device or system for delivering an endovascular prosthesis, the terms "proximal" and "proximally" shall denote a position, direction, or orientation that is generally toward, or in the direction of, the operator of the device or system. The terms "distal" and "distally" in this context shall denote a position, direction, or orientation that is generally opposite "proximal" or "proximally," or in a direction toward, or in the direction of, the patient.

The term "end" when used with respect to a structure refers broadly to a final, terminal, or extreme part, portion, or length of the structure. For example, the distal end of a wire refers to a distal part, portion, or length of a wire.

The term "stent" means any device or structure that provides or is configured to provide rigidity, expansion force, or support to a body part, for example, a diseased, damaged, or otherwise compromised body lumen. A stent may comprise any suitable biocompatible material, including, but not limited to fabrics, metals, plastics, and the like. Examples of suitable materials include metals such as stainless steel and nitinol, and plastics such as polyethylene terephthalate ("PET"), polytetrafluoroethylene ("PTFE") and polyurethane.

A stent may be "expandable," that is, it may be capable of being expanded to a larger-dimension configuration. A stent may expand by virtue of its own resilience (i.e., self-expanding), upon the application of an external force (i.e., balloon-expandable), or by a combination of both. In one example, a stent may have one or more self-expanding portions and one or more balloon-expandable portions.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. A stent may be attached to or associated with a graft to form a "stent graft."

The term "vessel" refers to a tube, cavity, duct, or canal in which fluid may be contained and conveyed or circulated. A body vessel (as opposed to a prosthetic vessel) is a vessel that exists naturally, or is formed naturally in the body. Examples of body vessels include, but are not limited to, blood vessels such as the aorta and the femoral artery, the esophagus, the trachea, the ureter, the bile duct, and the like. Examples of prosthetic vessels include, but are not limited to, stents, grafts, stent grafts, venous or aortal valves, vena cava filters, and the like.

The term "lumen" describes a space within a vessel in which fluid may be contained, conveyed, and/or circulated. The term "endoluminal" means within a lumen, and can refer to objects that are found or that can be placed within a lumen, or methods or processes that occur within a lumen. An "endoluminal prosthesis" is a prosthesis that is found or that can be placed within a lumen. Examples of endoluminal prostheses include, but are not limited to, stents, grafts, stent grafts, venous or aortal valves, vena cava filters, and the like. An endoluminal prosthesis may be generally tubular and comprise one or more lumens. Examples of tubular prostheses include, but are not limited to, straight, curved, branched, and bifurcated prostheses.

Figure 2A:
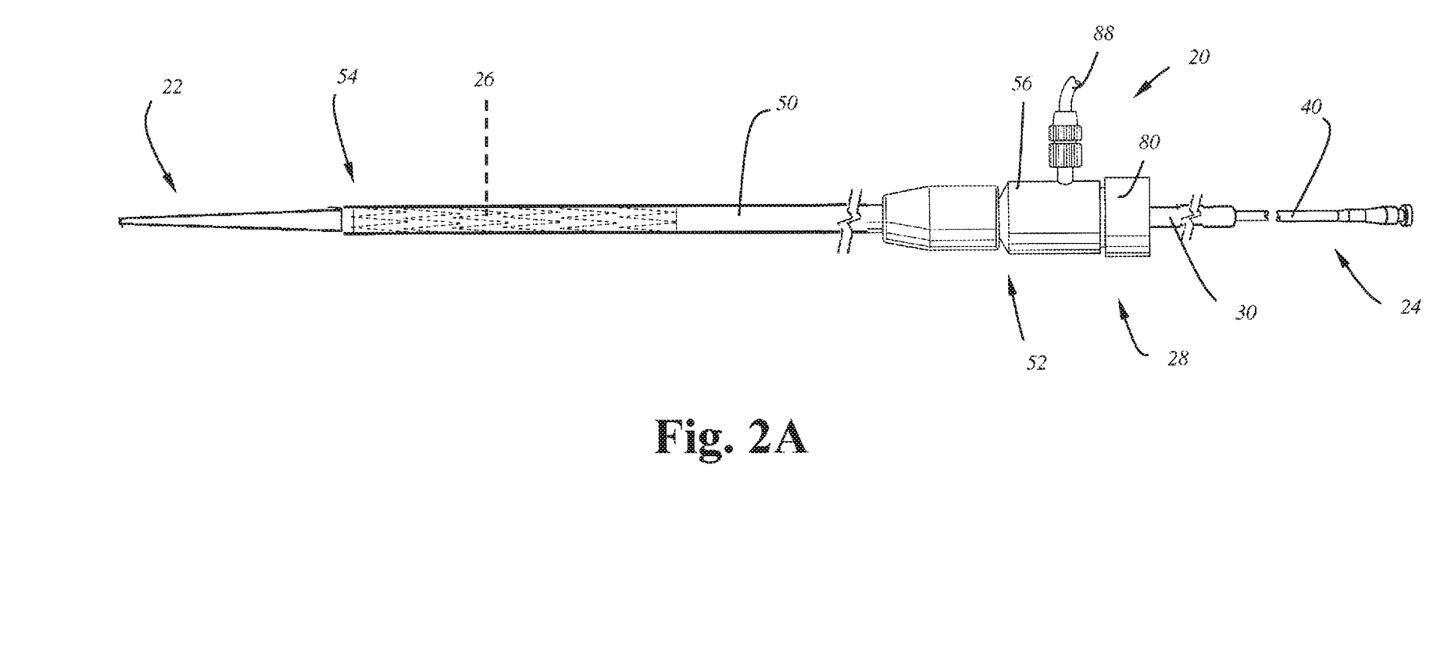
FIGS. 2A and 2B depict side views of an example of a delivery and deployment device, in accordance with the teachings of this specification.
Figure 2B:
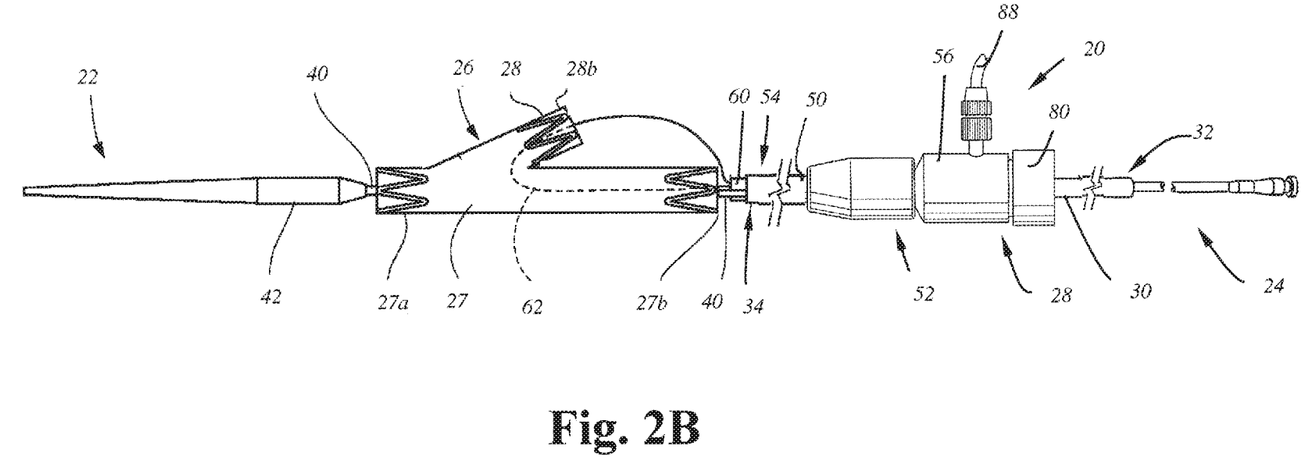

FIGS. 2A and 2B depict an example of a prosthesis delivery and deployment device 20. The device 20 has a distal end 22, which is inserted into a patient during a procedure, and a proximal end 24, which remains outside of the patient throughout the procedure. A stent graft 26 is disposed at a distal end portion of the delivery and deployment device 20. A handle portion 28 is disposed at a proximal end portion of the delivery device 20 and may be manipulated by the operator during the procedure.

In a preferred example shown in FIG. 2B, the stent graft 26 has a branched configuration with a tubular main body portion 27 and a branch portion 28. The main body portion 27 extends distally between a proximal end 27a and a distal end 27b. The side branch portion 28 extends distally from the main body portion 27 to a distal end 28b. The stent graft 26 in this example may be configured to be deployed into the vasculature of a patient with the main body portion 27 located in a common iliac artery and the side branch portion 28 directed towards an internal iliac artery of the common iliac artery. Other prostheses and configurations are contemplated within the scope of the present invention.

The delivery and deployment device 20 is preferably "preloaded," or pre-assembled with mechanisms to facilitate prosthesis delivery and deployment. These mechanisms may include, for example, one or more guide wires, catheters, sheaths, stents, stent grafts, and combinations thereof, which are arranged on and/or are carried by the device 20 and which remain in place during delivery of the stent graft 26 into a patient's vasculature. In one non-limiting example, the delivery and deployment device 20 may include one or more mechanisms that aid in the placement and deployment of a stent graft 26 in a common iliac artery and/or one or more mechanisms that aid in the placement and deployment of an additional or side branch extension stent grafts in an internal iliac artery in accordance with the systems and methods described herein.

The device in FIGS. 2A and 2B includes a pusher catheter 30 having a proximal end 32 and a distal end 34. The pusher catheter 30 has one or more lumens extending between the proximal 32 and distal ends 34. A guide wire catheter 40 extends through a lumen of the pusher catheter 30, from the proximal end of the device 24 (the end manipulated by the operator) to nose cone dilator 42 at the distal end of the device 22 (the end inserted into the patient).

A sleeve or sheath 50 is preferably mounted co-axially over the pusher catheter 30 and extends between a proximal end 52 and a distal end 54. A handle 56 is coupled to the proximal end of the sheath 50. The handle 56 may include a haemostatic sealing means 80 for controlling blood loss through the delivery and deployment device 20.

FIG. 2A shows a pre-deployment configuration, in which the stent graft 26 is arranged within a distal end of the sheath 50, about a distal end portion of the guide wire catheter 40. In this configuration the proximal end of the stent graft 26 is disposed adjacent the proximal end of the nose cone dilator 42, and the distal end of the stent graft is disposed adjacent the distal end of the pusher catheter 30. The stent graft 26 may be disposed entirely within the distal end 54 of the sheath 50 in a pre-deployment configuration, as shown in FIG. 2A. Alternatively, the sheath 50 may be disposed only partially within the distal end 54 of the sheath 50 in a pre-deployment configuration.

FIG. 2B depicts a deployment configuration of the device 20, in which the stent graft 26 is partially deployed and the sheath 50 has been withdrawn to show detail of the assembly. The sheath 50 may be withdrawn from the stent graft 26 by sliding the handle 56 proximally with respect to the pusher catheter 30, thereby moving the sheath proximally with respect to the stent graft 26.

As shown in FIG. 2B, the delivery and deployment device 20 may further include an auxiliary sheath 60 and guide wire 62 extending through a lumen of the pusher catheter 30, for facilitating placement and deployment of the side branch portion 28 of the stent graft 26. These and other mechanisms for facilitating placement and deployment of the stent graft can be found, for example, in U.S. Patent Publication No. 2014/0277330 A1, incorporated herein by reference.

The delivery and deployment device 20 preferably includes a wire retention and release mechanism to retain the stent graft 26 during delivery and deployment. The wire retention and release mechanism includes at least one wire having first and second ends, and a body portion disposed therebetween. The first end of the wire is releasably coupled to the stent graft 26 in a release arrangement, and the second end of the wire is coupled to the sheath 50. The stent graft 26, wire, and sheath 50 are arranged so that a movement of the sheath 50 relative to the stent graft 26 decouples the wire from the stent graft.

Figures 3A, 3B, 4A, 4B:
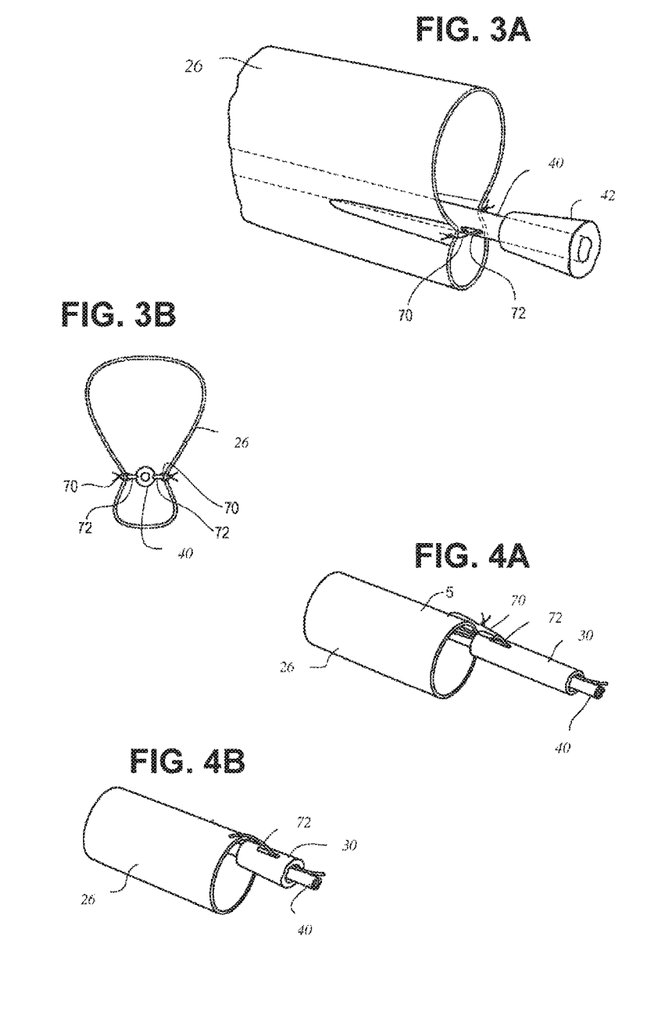
FIGS. 3A and 3B depict side perspective and end views of an example of a wire release arrangement, in accordance with the teachings of this specification.
FIGS. 4A and 4B depict side perspective views of other examples of wire release arrangements, in accordance with the teachings of this specification.

FIGS. 3A and 3B depict an example of a suitable wire release arrangement in accordance with the teachings of U.S. Patent Publication No. 2014/0277330 A1. In the arrangement shown in FIGS. 3A and 3B, one or more trigger wires 72 releasably couple a proximal end portion of the stent graft 26 to the guide wire catheter 40 via optional loops or stitches of suture material 70. FIGS. 4A and 4B depict another suitable wire release arrangement for releasably coupling the stent graft 26 to the delivery device 20. In the arrangement shown in FIGS. 4A and 4B, one or more trigger wires 72 releasably couple a distal end portion of the stent graft 26 to the pusher catheter 30. In FIG. 4A, the stent graft 26 is coupled to the pusher catheter 30 via one or more sutures 70. In FIG. 4B, instead of using sutures the trigger wire 72 engages directly with the stent graft 26.

Other release arrangements are contemplated and include one or more trigger wires releasably coupled to one or more portions of the stent graft 26. In each example, the stent graft 26 is retained until the trigger wire or wires are released. It is contemplated that other types and methods of restraint may be used including various diameter reducing ties, fasteners or the like that are suitable for removably securing the stent graft 26 on the delivery device 20.

The second end of the wire 72 may be coupled to the sheath 50 in any suitable manner. In the examples shown in FIGS. 5 and 6, the proximal end of the trigger wire 72 is coupled to handle 56 of the sheath 50. The stent graft 26, wire, and sheath 50 are arranged so that a proximal movement of the sheath 50 relative to the stent graft 26 (e.g., by sliding the handle 56 proximally), both: 1) withdraws the sheath 50 from the stent graft 26; and 2) decouples the wire 72 from the stent graft 26.

Figure 5A:
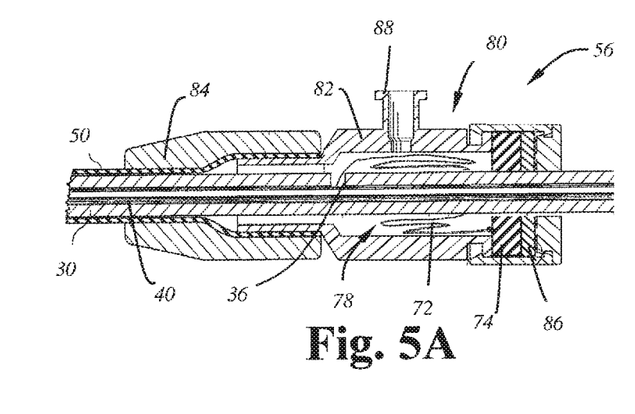
FIGS. 5A and 5B depict cross-sectional views of a proximal portion of a sheath and trigger wire, in accordance with the teachings of this specification.
Figure 5B:
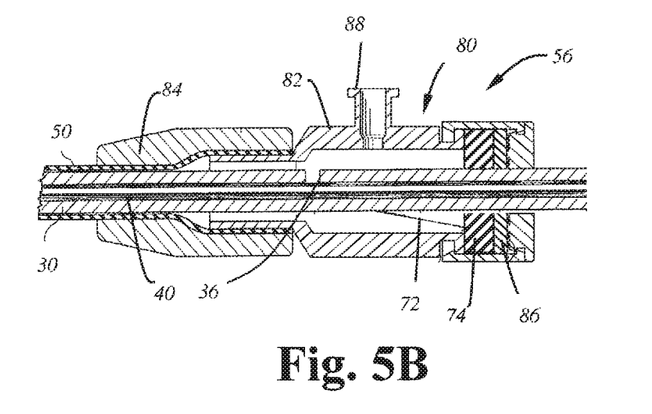
Figure 6A:
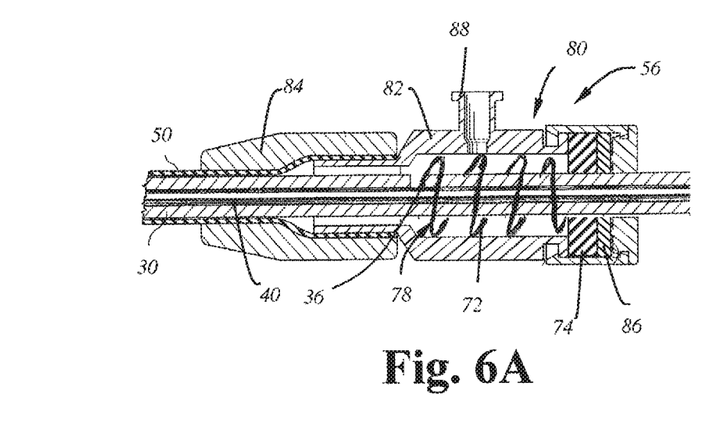
FIGS. 6A and 6B depict additional cross-sectional views of a proximal portion of a sheath and trigger wire, in accordance with the teachings of this specification.
Figure 6B:
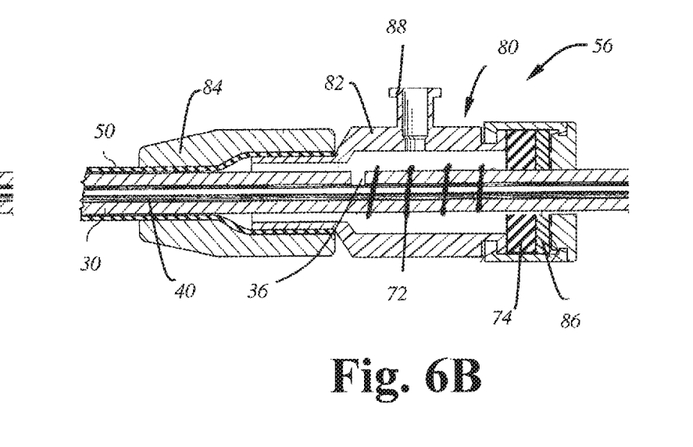

The handle 56 shown in FIGS. 5 and 6 comprises haemostatic sealing means 80, including a haemostatic housing 82. Clamping collar 84 couples the distal end of the housing 82 to the proximal end of the sheath 50. The sealing means 80 further comprises one or more haemostatic valves 86, which in use provide a haemostatic seal between the sheath 50 and the pusher catheter 30. Suitable haemostatic valves include, for example, disk valves, iris valves, and the like. The haemostatic sealing means 80 may also include a side tube 88 to facilitate the introduction of medical reagents between the pusher catheter 30 and the sheath 50. U.S. Pat. Nos. 6,416,499 and 7,651,519, and U.S. Patent Application Publication Nos. 2005/0171479 A1 and 2007/0078395 A1 describe examples of suitable haemostatic sealing devices that can be used with the devices, systems, and methods described in the present application. Each of these patent references is incorporated by reference herein in its entirety.

FIG. 5A depicts handle 56 in a pre-deployment configuration, corresponding generally with the pre-deployment configuration shown in FIG. 2A. The stent graft 26 is disposed within the distal end 54 of the sheath 50. Trigger wire 72 is coupled to the stent graft 26 at the distal end of the wire, and extends proximally through a lumen of the pusher catheter 30 into haemostatic housing 82 via aperture 36 in the pusher catheter 30. The proximal end of the trigger wire 72 is coupled to trigger wire collar 74 disposed within the haemostatic housing 82.

In the configuration shown in FIG. 5A, the trigger wire 72 comprises a slack 78 in the wire 72, characterized by an excess of wire within the housing 82. The slack 78 may be reduced by pulling the distal and proximal ends of the trigger wire 72 away from one another. For example, the slack 78 in FIG. 5A may be reduced by sliding the handle 56 proximally with respect to the stent graft 26, thereby moving the proximal end of the trigger wire 72 proximally both with respect to the stent graft 26 and the distal end of the trigger wire coupled to the stent graft. FIG. 5B depicts the handle 56 of FIG. 5A with the slack 78 removed. In this configuration, the trigger wire 72 is taut, so that sliding the handle 56 proximally with respect to the stent graft 26 will move the distal end of the trigger wire 72 proximally with respect to the stent graft 26, thereby decoupling the wire from the stent graft.

FIG. 6A depicts handle 56, with the slack 78 in the wire 72 characterized by an excess of wire 72 wound within the housing 82. The slack 78 may be reduced, for example, by sliding the handle 56 proximally with respect to the stent graft 26, thereby moving the proximal end of the trigger wire 72 proximally both with respect to the stent graft 26 and the distal end of the trigger wire coupled to the stent graft. FIG. 6B depicts the handle 56 of FIG. 6A with the slack 78 removed. The trigger wire 72 is taut, so that sliding the handle 56 proximally with respect to the stent graft 26 will decouple the wire from the stent graft.

Housing 82 may be formed of a relatively hard polymeric material, such as acetal, polypropylene, ABS, nylon, PVC, polyethylene or polycarbonate. In some examples, the housing 82 may be formed of a material that is transparent, to allow the operator to view the trigger wire 72 and any slack 78 during the procedure. On the other hand, the housing 82 may be formed of an opaque material if viewing the trigger wires in the handle is undesirable.

Figure 7:
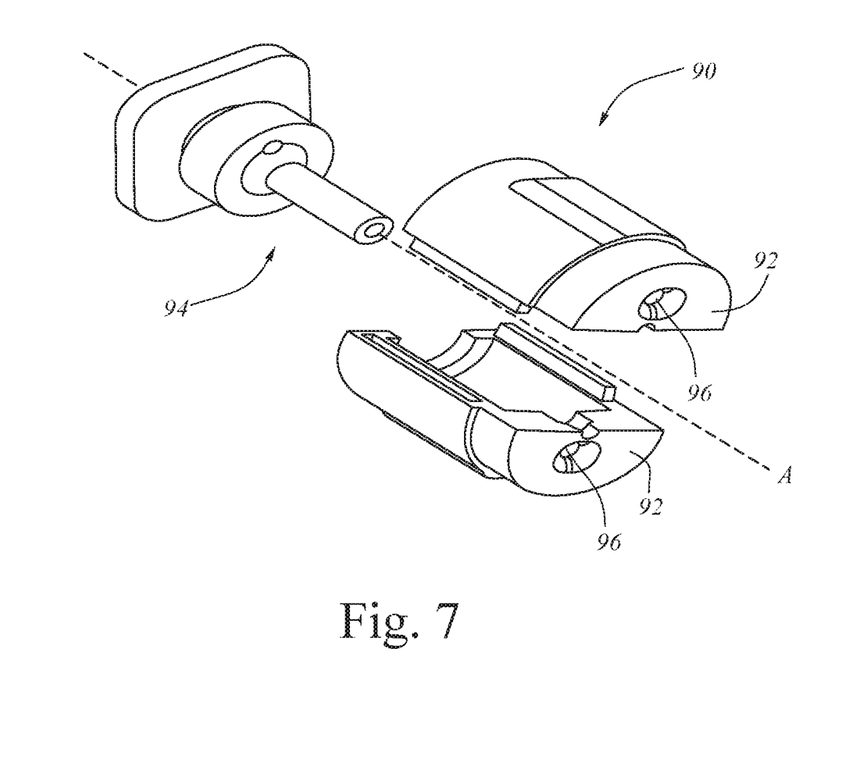
FIG. 7 depicts an exploded perspective view of a wire drum mechanism, in accordance with the teachings of this specification.

FIG. 7 depicts a wire drum mechanism 90 that may be used in connection with the foregoing examples. The mechanism 90 includes a housing 92, and a drum 94 disposed within the housing. The drum 94 may be rotatable about an axis A of the housing 92. The drum mechanism 90 may be coupled to the sheath, for example the proximal end of the sheath 50 (in conjunction with or as part of the handle 56), and configured to store and release slack in one or more trigger wires. In one example, two or more wires 72 may be provided, each with a distal end coupled to stent graft 26, a proximal end coupled to a handle with a drum mechanism 90, and a slack in the wire 78 wound about drum 94. In the pre-deployment configuration, the wires 72 extend proximally from the distal end of the stent graft 26 and into the drum housing 92 through apertures 96 in the housing. The slack in the wires may be reduced, for example, by sliding the handle 56 and drum mechanism 90 proximally with respect to the stent graft 26, thereby allowing the wires 72 to unwind from the drum 94.

In each of the foregoing examples, the slack of a trigger wire may be selected to correspond with a length of the prosthesis. In one example, the slack may be selected to correspond with approximately 10% or more of the length of the prosthesis, such that the trigger wire will become taut after the sheath has been withdrawn a distance of approximately 10% or more of the length of the prosthesis. In other examples, the slack may be selected to correspond with approximately 20% or more, approximately 50% or more, or approximately 75% or more of the length of the prosthesis.

With respect to the branched stent graft 26 depicted in FIG. 2B, the slack may be selected so that the trigger wire will become taut before sheath 50 has been withdrawn from branch portion 28, after sheath 50 has been withdrawn from branch portion 28, or after sheath 50 has been withdrawn entirely from the stent graft 26. In some examples, a wire retention and release mechanism may include a plurality of wires, each having first ends coupled to the stent graft 26 and second ends coupled to the sheath 50. The wires may be releasably coupled to the stent graft 26 in one or more release arrangements, and at one or more positions along the length of the graft. For example, one or more wires may be coupled to a proximal end of the stent graft 26, one or more wires may be coupled to a distal end of the stent graft 26, or both.

In devices with more than one trigger wire, at least one of the wires may include a slack in the wire in a pre-deployment configuration. In some examples, at least two wires are provided and include slacks that are generally equal. In other examples, one of the wires has a slack that is greater than the slack of the other of the wires. For example, with respect to the device depicted in FIG. 2, the slack in a first trigger wire may be selected so that the first wire will become taut before sheath 50 has been withdrawn from branch portion 28, and the slack in a second trigger wire may be selected so that the second wire will become taut after sheath 50 has been withdrawn entirely from the stent graft 26.

Figure 8:
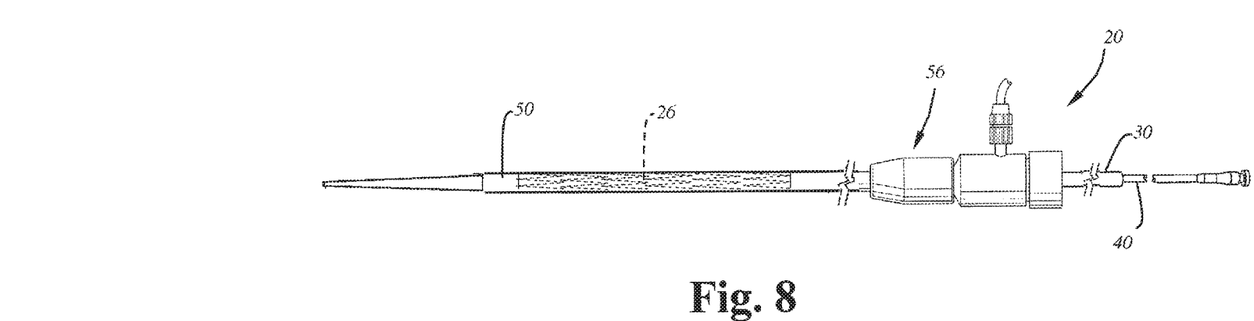
FIGS. 8-10 depict various stages of a method of deploying a delivery and deployment device, in accordance with the teachings of this specification.
Figure 9:
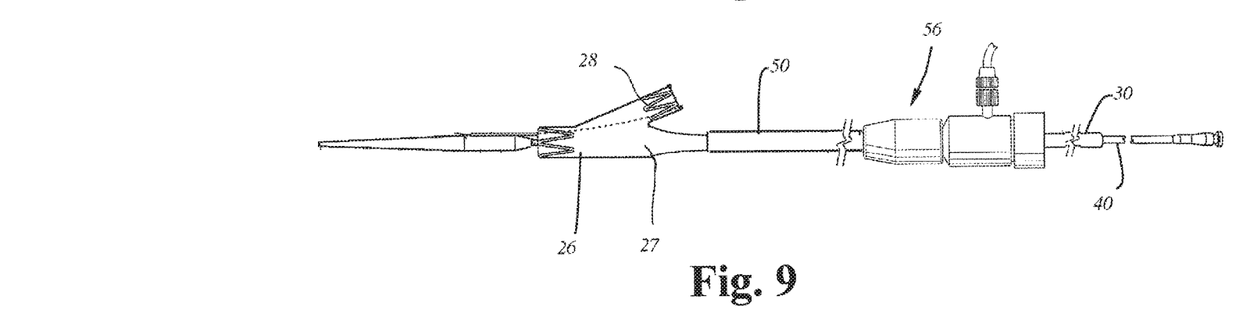
Figure 10:
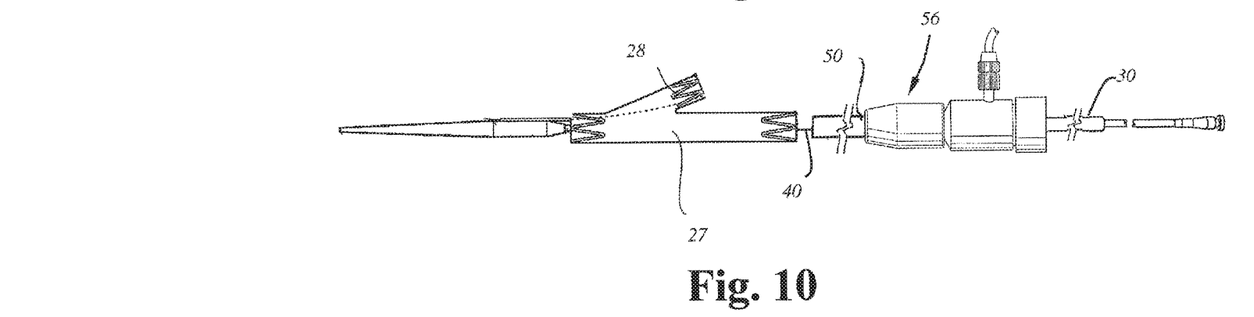

FIGS. 8-10 depict various stages of an example of a method for delivering and deploying a prosthesis using a delivery and deployment device described above. Although the method is described in relation to a stent graft for treating the vasculature, it can readily be applied to other prostheses and indications.

A delivery and deployment device 20 as described with respect to FIGS. 2A and 2B is provided, and comprises a pusher catheter 30 and a guide wire catheter 40 slidingly disposed within an axial lumen of the pusher catheter. The pusher catheter 30 is slidingly disposed within an axial lumen of sheath 50. Stent graft 26 is disposed over a distal end portion of the device 20, within the distal end of sheath 50. Stent graft 26 has a branched configuration, including a tubular main body portion 27 and a branch portion 28.

The delivery and deployment device 20 includes a wire retention and release mechanism. The mechanism includes at least one wire 72 having first and second ends, and a body portion disposed therebetween. The first end of the at least one wire 72 is releasably coupled to the stent graft 26 in a suitable release arrangement, such as an arrangement described above with respect to FIGS. 3 and 4. The second end of the at least one wire 72 is coupled to the sheath 50. In the present example, the second end of the at least one wire 72 is coupled to handle 56, as described above with respect to FIGS. 5-7.

Although not shown in FIGS. 8-10, the delivery and deployment device 20 may include additional mechanisms to aid in the placement and deployment of the stent graft 26, such as auxiliary sheaths and guide wires for facilitating placement and deployment of the side branch portion 28 of the stent graft 26, as described above.

FIG. 8 depicts the delivery and deployment device 20 disposed in a pre-deployment configuration. In this configuration, the at least one wire 72 has a slack 78 (see, e.g., FIGS. 5A and 6A). Device 20 may be delivered within a vessel in a conventional manner. A guide wire (not shown) may be introduced, for example, into a femoral artery and advanced into the vessel until the tip of the guide wire extends beyond the region in which the stent graft 26 will be placed. The delivery and deployment device 20 is then inserted over the guide wire, via guide wire catheter 40, into the vessel and positioned by radiographic techniques generally known in the art.

At this stage, the stent graft 26 is disposed in a compressed configuration within the distal end of the sheath 50. Once the device 20 is in a desired position, the sheath 50 may be retracted proximally to expose the proximal end of the stent graft 26 (the end closest to the patient's heart). This action releases the proximal end of the stent graft 26 so that it can expand radially outwardly, as shown in FIG. 9. In addition, this action moves the second end of the at least one wire 72 proximally with respect to the stent graft 26 and the first end of the at least one wire, thereby reducing the slack 78 until the at least one wire is taut (as shown in FIGS. 5B and 6B).

At this stage, the distal end of the stent graft 26 (the end furthest from the patient's heart) is still retained within the distal end of the sheath 50 (the end furthest from the operator). In addition, the stent graft 26 is still retained by the at least one wire 72. The sheath 50 may be retracted further proximally to expose and release the distal end of the stent graft 26 from the sheath 50, as shown in FIG. 10. Because the wire is now taut, this action moves both the first and second ends of the at least one wire 72 proximally with respect to the stent graft 26, thereby decoupling the wire from the stent graft.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together.

The invention claimed is:

1. A prosthesis delivery and deployment device comprising:
    a sheath having a proximal end, a distal end, and a lumen extending between the proximal and distal ends;
    a prosthesis disposed within a distal end portion of the sheath; and
    a first wire having a first end coupled to the prosthesis, a second end coupled to the sheath, and a body portion disposed between the first and second ends, the body portion comprising a slack in the first wire;
    where the sheath, prosthesis, and wire are configured so that a proximal movement of the sheath relative to the prosthesis reduces the slack in the first wire, and a first subsequent proximal movement of the sheath relative to the prosthesis decouples the first wire from the prosthesis.

2. The device of claim 1, where the second end of the first wire is coupled to a handle of the sheath.

3. The device of claim 2, where the handle is disposed at the proximal end of the sheath.

4. The device of claim 2, where the handle comprises a drum, and the slack is wound about the drum.

5. The device of claim 2, where the handle comprises a haemostatic valve.

6. The device of claim 1, where the prosthesis is disposed entirely within the distal end of the sheath.

7. The device of claim 1, where the slack corresponds with a length of the prosthesis.

8. The device of claim 7, where the slack corresponds with approximately 10% or more of the length of the prosthesis.

9. The device of claim 7, where the slack corresponds with approximately 50% or more of the length of the prosthesis.

10. The device of claim 1, further comprising:
a second wire having a first end coupled to the prosthesis, a second end coupled to the sheath, and a body portion disposed between the first and second ends, the body portion of the second wire comprising a slack in the second wire;
where the sheath, prosthesis, and second wire are configured so that the proximal movement of the sheath relative to the prosthesis reduces the slack in the second wire, and the first or a second subsequent proximal movement of the sheath relative to the prosthesis decouples the second wire from the prosthesis.

11. The device of claim 10, where the first wire slack and the second wire slack are generally equal.

12. The device of claim 10, where the second wire slack is greater than the first wire slack.

13. The device of claim 10, where the first end of one of the first and second wires is coupled to the proximal end of the prosthesis and the first end of the other of the second and first wires is coupled to the distal end of the prosthesis.

14. The device of claim 10, where the sheath, prosthesis, first wire, and second wire are configured so that the proximal movement of the sheath relative to the prosthesis reduces the slack in the first and second wires, the first subsequent proximal movement of the sheath relative to the prosthesis decouples the first wire from the prosthesis and further reduces the slack in the second wire, and a second subsequent proximal movement of the sheath relative to the prosthesis decouples the second wire from the prosthesis.

15. A prosthesis delivery and deployment device comprising:
a sheath having a proximal end, a distal end, and a lumen extending between the proximal and distal ends;
a haemostatic valve assembly coupled to the proximal end of the sheath;
a prosthesis disposed within a distal end portion of the sheath;
a wire having a first end coupled to the prosthesis, a second end coupled to the valve assembly, and a body portion disposed between the first and second ends of the wire;
where the body portion of the wire comprises a slack in the wire; and
where the sheath, valve assembly, prosthesis, and wire are configured so that proximal movement of the valve assembly relative to the prosthesis retracts the sheath and decouples the wire from the prosthesis; and
further comprising a drum, where the slack is wound about the drum.

16. The device of claim 15, where the wire is configured so that the proximal movement of the valve assembly relative to the prosthesis reduces the slack in the wire, and a first subsequent proximal movement of the valve assembly relative to the prosthesis decouples the wire from the prosthesis.

17. The device of claim 15, further comprising a second wire having a first end coupled to the prosthesis, a second end coupled to the valve assembly, and a body portion disposed between the first and second ends, where the sheath, valve assembly, prosthesis, and second wire are configured so that the proximal movement or a first or second subsequent proximal movement of the valve assembly relative to the prosthesis decouples the second wire from the prosthesis.

18. The device of claim 17, where the first end of one of the first and second wires is coupled to the proximal end of the prosthesis and the first end of the other of the second and first wires is coupled to the distal end of the prosthesis.

* * * * *